United States Patent
Schoeppe et al.

(10) Patent No.: US 7,223,369 B2
(45) Date of Patent: May 29, 2007

(54) AUTOMATIC TIP CHANGER FOR AUTOMATIC MULTIPIPETTORS

(75) Inventors: Torsten Schoeppe, Jena (DE); Frank Tempel, Jena (DE)

(73) Assignee: CyBio AG, Jena (DE)

( * ) Notice: Subject to any disclaimer, the term of this patent is extended or adjusted under 35 U.S.C. 154(b) by 507 days.

(21) Appl. No.: 10/224,137

(22) Filed: Aug. 19, 2002

(65) Prior Publication Data
US 2003/0037624 A1     Feb. 27, 2003

(30) Foreign Application Priority Data
Aug. 23, 2001   (DE) ............................ 201 14 052 U (51) Int. Cl.
*B01L 3/02*       (2006.01)
*G01N 21/00*      (2006.01)
(52) U.S. Cl. ..................... 422/100; 422/63; 422/64; 422/99; 422/104
(58) Field of Classification Search ............... 422/99, 422/100, 102, 104, 63, 64, 67; 73/863.31
See application file for complete search history.

(56) References Cited
U.S. PATENT DOCUMENTS 5,332,549 A * 7/1994 MacIndoe, Jr. ............... 422/63
5,928,952 A * 7/1999 Hutchins et al. ............... 436/50
5,955,373 A * 9/1999 Hutchins et al. ............... 436/48
6,669,432 B2 * 12/2003 Hamel et al. ........... 414/331.05

* cited by examiner

*Primary Examiner*—Brian R. Gordon
(74) *Attorney, Agent, or Firm*—Reed Smith LLP (57) ABSTRACT

An automatic tip changer for an automatic multichannel pipettor comprises a plurality of pipettes arranged in a pipetting head. Each of the pipettes arranged in the pipetting head is directly connected to a tip. A magazine which is outfitted with tips and lying in a magazine frame is pressed against the pipetting head. A supply carousel is provided for storing a plurality of stacking boxes in which magazines outfitted with tips are deposited. A lifting group which is arranged in a stationary manner relative to the supply carousel and the magazines are positioned successively in a mounting plane which is determined by the position of the magazine frame. A sliding group is included which is arranged in a stationary manner relative to the lifting group and by which the magazines are displaceable back and forth successively between the stacking box and the magazine frame.

3 Claims, 12 Drawing Sheets

AUTOMATIC TIP CHANGER FOR AUTOMATIC MULTIPIPETTORS

CROSS-REFERENCE TO RELATED APPLICATIONS

This application claims priority of German Application No. 201 14 052.7, filed Aug. 23, 2001, the complete disclosure of which is hereby incorporated by reference.

BACKGROUND OF THE INVENTION a) Field of the Invention

The invention relates to an automatic tip changer for automatic multipipettors.

b) Description of the Related Art

Automatic multichannel pipettors can be distinguished basically by the way that the pipettes arranged in the pipetting head are connected with the associated pipette tips (tips), i.e., those with a frictional-positive connection and those with a purely frictional connection between the open ends of the pipettes and the receiving openings of the tips.

Of these two groups, the CyBi™-Well 96, CyBi™-Well 384 and CyBi™-Well 1536 automatic pipettors manufactured by CyBio AG belong to the latter. These automatic pipettors have a pipetting head with 96 or 384 pipettes which are arranged in a 8×12 format and 16×24 format, respectively, and whose open ends open into a plane surface oriented perpendicular to the respective pipette axis. A plate-shaped elastomer seal is placed on the plane surfaces of all pipette ends in common and, in accordance with the grid or format of the pipettes, has openings with a diameter equal to the open ends of the pipettes.

In order to connect the pipettes to a tip, a tip magazine (magazine) outfitted with tips is pressed against the elastomer seal. In order to position the receiving openings of the tips relative to the open ends of the pipettes, the loaded magazine is inserted as far as a stop into a sliding guide (magazine frame 35) located at the pipetting head and the magazine frame 35 is then lifted toward the pipetting head, so that the receiving openings of the tips tightly contact the elastomer seal. To remove the magazine, the magazine frame 35 is lowered again, so that the indirect frictional connection between the open end of the pipettes and the receiving openings of the tips is detached. Changing magazines was formerly carried out manually in the CyBi™-Well.

There are also other known automatic multichannel pipettors in which the tips and the magazines outfitted with tips are changed automatically.

OBJECT AND SUMMARY OF THE INVENTION

Therefore, it is the primary object of the invention to propose a device for automatic, computer-assisted changing of magazines outfitted with tips for an automatic multichannel pipettor as a substitute for the exclusively manual changing of magazines which was formerly customary. Further, compared to the free space which was formerly required for manual changing, the device according to the invention does not occupy a lot of space in the working area of a laboratory equipment installation comprising an automatic multichannel pipettor with peripheral laboratory equipment such as washing apparatus, measuring apparatus and incubators which are interconnected by a transporting device. Further, the device according to the invention is suitable for retrofitting automatic multichannel pipettors in existing laboratory equipment systems with a device of this type. In addition, the device serves as a storage for the unused and used magazines so that contamination of unused magazines by used magazines is prevented. Further, the device is suitable for different types of magazine.

The object according to the invention is met by an automatic tip changer for an automatic multichannel pipettor comprising a supply carousel for storing a plurality of stacking boxes in which magazines outfitted with tips are placed, a lifting group which lifts the stacking boxes out of the supply carousel one after the other and positions the magazines successively in a mounting plane which is determined by the position of the magazine frame, and a displacing or sliding group which displaces the magazines successively back and forth between the stacking box and the magazine frame.

It is essential to the invention that the magazines supported in a stacking box, including the stacking box, are transported until directly in front of the magazine frame, so that the actual time for exchanging the tips can be kept very short and the tip changer is suitable for different types of magazine. The magazine types differ with respect to the quantity, length and volume of the tips with which they are outfitted. The magazines are aligned in the stacking boxes by means of stops which are not located at the stacking boxes themselves. Therefore, the stacking boxes can be kept completely open on both of the sides on which the stacking boxes are manually and automatically loaded and removed. The exchanging of tips at the automatic multichannel pipettor and the loading of the supply carousel are two processes which take place separately from one another, so that the tips can be changed at the same time that the supply carousel is loaded and unloaded. The automatic tip changer is therefore permanently operational.

The invention will be described more fully in the following by an embodiment example with reference to the drawings.

DESCRIPTION OF THE PREFERRED EMBODIMENTS

Figure 7:
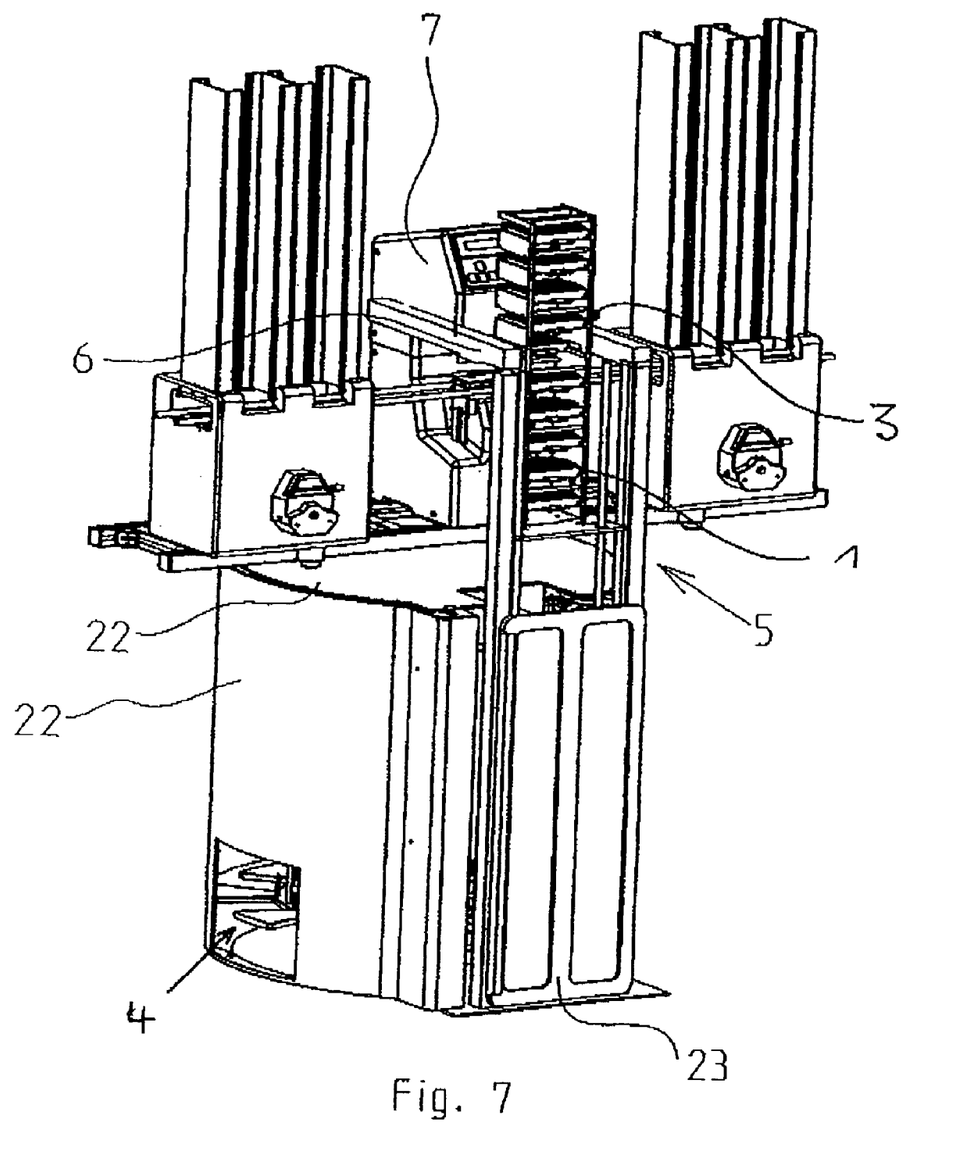
FIG. 7 is a schematic view of a tip changer arranged at an automatic multichannel pipettor with laboratory equipment advanced toward it.

As is shown in FIG. 7, an automatic tip changer according to the invention essentially comprises a supply carousel 4 for storing stacking boxes 3 which are outfitted with magazines 1, a lifting group 5 for transporting the stacking boxes 3 in the work area of the automatic multichannel pipettor 7 to be operated, and a sliding group 6 for horizontal positioning of a magazine 1 relative to the pipetting head of an automatic multichannel pipettor 7.

Figure 1:
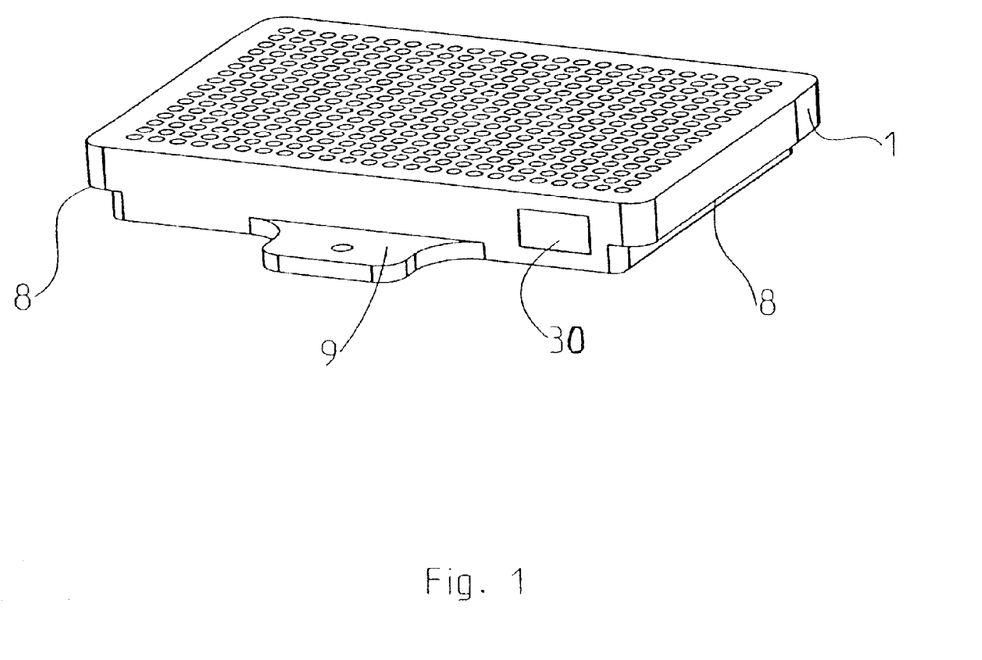
FIG. 1 shows a magazine for 384 tips arranged in a 16×24 format.

FIG. 1 shows a magazine 1 for a quantity of 384 tips 2. The outer dimensions of the magazines are identical regardless of the quantity, volume and length of the attachable tips 2 and have two guide paths 8 on two opposite edges. The dimensioning of a magazine frame 35 arranged at the automatic multichannel pipettor 7 for receiving the magazines 1 is suitably adapted, so that a magazine 1 is deposited so as to be exactly positioned with respect to the pipette arrangement in the pipetting head by guiding in a sliding manner with, at most, a slight lateral play. As was already described, this is carried out manually in the art. For this purpose, the operator holds the magazine 1 by a handle 9 provided for this purpose and inserts the magazine 1 into the above-mentioned magazine frame 35 as far as the stop. Usually, this magazine frame 35 is not located at eye level, so that the operator, if not in a sitting position, would have to assume a stooping posture. With an automatic tip changer according to the invention, the magazine feed is automated. The operator need only outfit the stacking boxes 3 with the magazine 1 or remove the used magazines 1 from the stacking boxes 3 and replace them with fresh magazines 1. This procedure can be carried out for a large number of magazines immediately one after the other depending on the planned storage capacity of the supply carousel 4 which, in the present embodiment example, is provided for one hundred magazines 1. In particular, when it is necessary to change tips 2 often, the automatic tip changer saves a large amount of time on labor.

Figure 2:
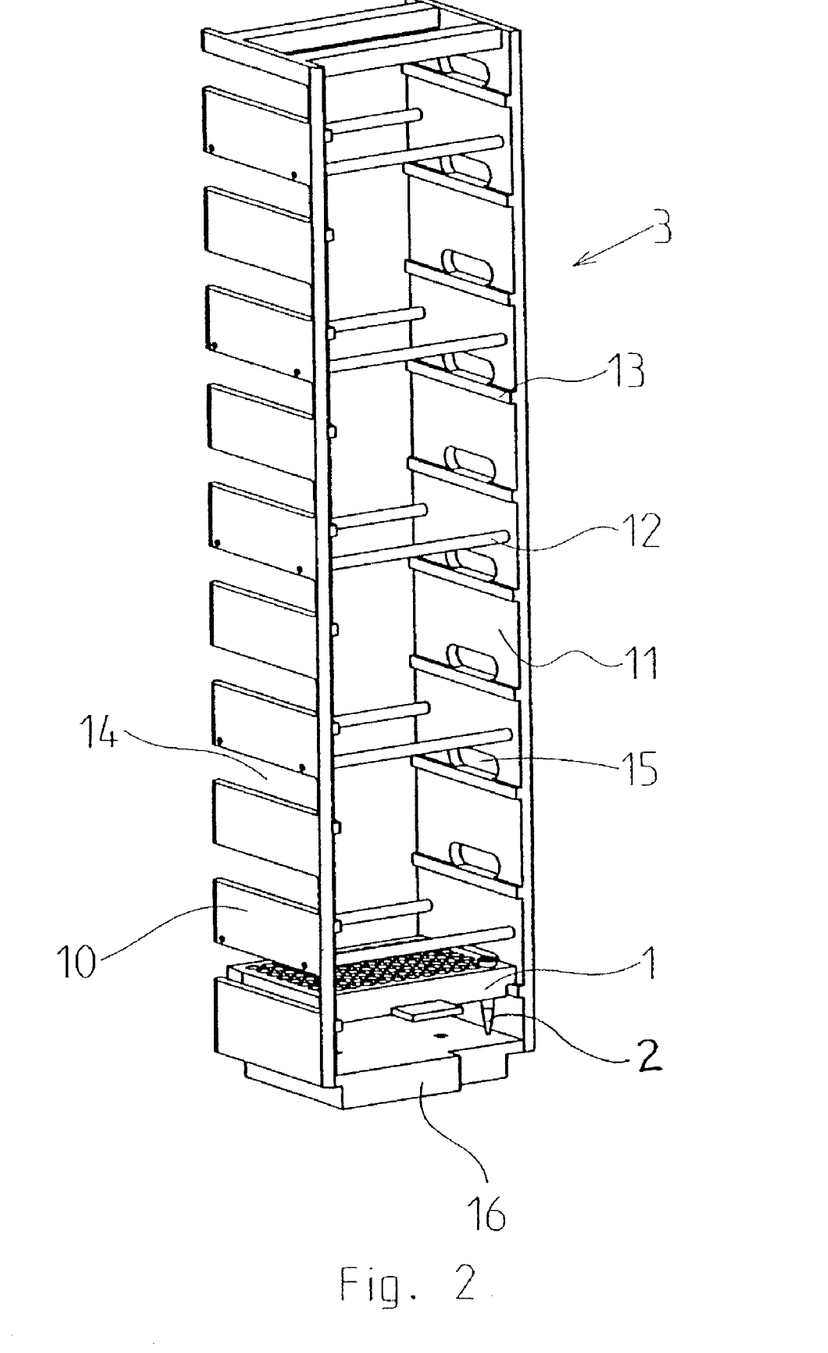
FIG. 2 shows a stacking box for 10 magazines.

FIG. 2 shows a stacking box 3 for ten magazines 1 outfitted with only one magazine 1. The stacking box 3 is rectangular and is formed by a first side wall 10 and an oppositely located second side wall 11 which are fixedly connected to one another by spacers 12 of identical length and have guide rails 13 which are located opposite one another in pairs for receiving the magazines 1. The distance between two successive guide rails 13 in vertical direction is determined depending on the space requirement for the magazine 1 outfitted with tips 2. This means that this distance must be greater for storing magazines 1 with longer tips 2 than when storing tips 2 of shorter length. The storage capacity of the stacking box 3 is maximized by providing different stacking boxes 3 in which the spacing between the guide rails is optimized for the actual space requirement for the respective type of magazine outfitted with tips 2. The different stacking boxes 3 are identical with respect to their outer dimensions. Essential functional features of the stacking box 3 are the open slot 14 which is located in the first side wall 10 above a guide rail 13, the through-holes 15 located in the second side wall 11 above a guide rail 13, and a specially shaped base plate 16. These features will be discussed more fully in connection with the description of the operation of the automatic tip changer. The stacking boxes 3 are completely open at the sides (front side and back side) between the side walls 10, 11 for outfitting the stacking boxes 3 with magazines 1 and aligning the latter, which will also be explained further on.

Figures 3A, 3B:
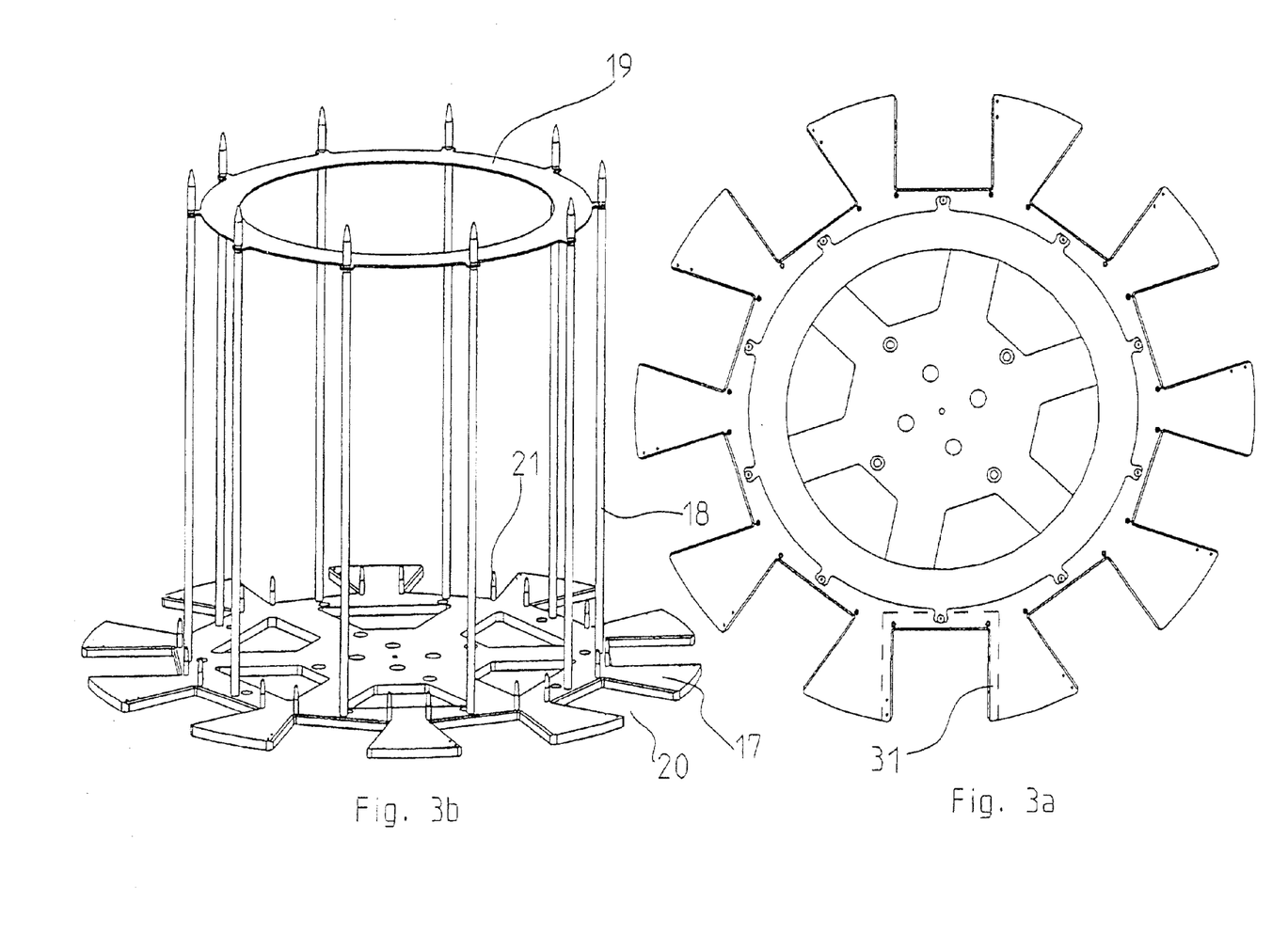
FIG. 3a is a top view showing a supply carousel for 10 stacking boxes.
FIG. 3b is a side view showing a supply carousel for 10 stacking boxes.

FIGS. 3a and 3b show a supply carousel 4, specifically for outfitting with ten stacking boxes 3, which essentially comprises a rotating disk 17, which is supported so as to be rotatable about an axis of rotation and which has ten depositing places 31 and ten stop bars 18 whose ends are fixedly clamped into the rotating disk 17 on one side and in a fixating ring 19 on the other side. The depositing places 31 are defined by cutouts 20 which open toward the circumference of the rotating disk 17, by the adjoining top surface area of the rotating disk 17, and by two positioning pins 21. The base plate 16 of the stacking boxes 3 and the cutouts 20 in the rotating disk 17 are adapted to one another with respect to contour in such a way that a stacking box 3 deposited on a depositing place 31 is secured in position horizontally up to a degree of freedom, that is, it can be displaced relative to the rotating disk 17 only in one direction (radial to the axis of rotation) and can not be turned. The cutouts 20 are rectangular in the present embodiment example. In a corresponding manner, the base plate 16 has an inner and an outer base plate part with bottom surfaced located in different planes. The inner base plate part is rectangular like the cutouts 20 with a slightly smaller cross section. Accordingly, when a stacking box 3 is placed on top, the plane bottom surface of the outer base plate part rests on the edge area of the cutout 20, while the base plate 16 is connected in a positive engagement with the rotating disk 17 by the cutout 20 along the circumference of the inner base plate part. The freedom of movement remaining in one direction radially is blocked by the two associated positioning pins 21 which are inserted into the base plate 16 in holes provided for this purpose.

The supply carousel 4 is accommodated in a cylindrical housing 22, shown in FIG. 7, which has a door opening in its circumferential surface for loading and removing the stacking boxes 3. In order to load the supply carousel 4, a free depositing place 31 is positioned in front of the door opening and a stacking box 3 outfitted with unused magazines 1 is deposited manually through the door opening on the lifter 27 which is positioned just above the rotating disk 17. The pins 29 located at the lifter 27 are inserted into holes which are provided for this purpose in the base plate 16 of the stacking box 3 and the stacking box 3 is accordingly aligned relative to the supply carousel 4. At the same time, a stop bar 18 engages in a recess provided in the base plate 16 for this purpose. A part of the magazines 1 not lying exactly in the center inside the stacking box 3 contacts the stop bar 18 and is displaced toward the center of the stacking box. When the lifter 27 is lowered into a position below the rotating disk 17 (zero position) in which the pins 29 no longer engage in the base plate 16, the stacking box 3 is deposited on a depositing place 31 on the rotating disk 17 and the positioning pins 21 are inserted into the base plate 16. The central alignment of all magazines 1 in the stacking box 3 is carried out by closing a door 23 arranged at the door opening until it is in a contact pressing position.

Figure 4:
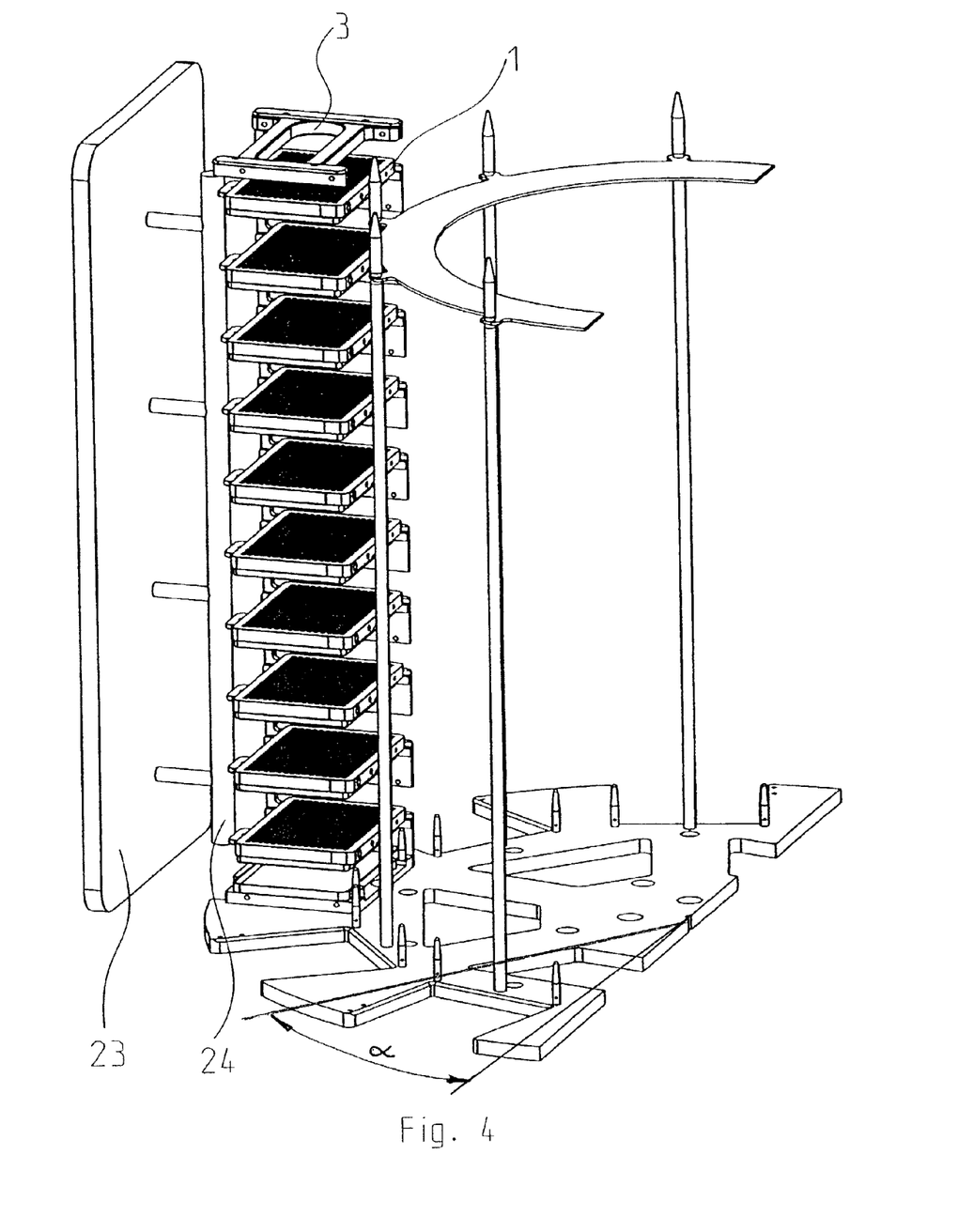
FIG. 4 is a partial view of a supply carousel outfitted with a stacking box with its door in the contact pressing position.

FIG. 4 shows a partial view of a supply carousel 4 which is outfitted with a stacking box 3 and which has a door 23 in the contact pressing position. The housing 22 of the supply carousel 4 and the second side wall 11 of the stacking box 3 have been omitted in this view. Accordingly, it can be seen clearly that the magazines 1 contact a stop bar 18 on the back side of the stacking box 3 and contact a stop bar 24 fastened to the door 23 on the front side of the stacking box 3. The door 23 which is fastened to the edge of the door opening in a springing manner remains in this contact pressing position until the door 23 is pushed closed by the operator and then returns to a closed position so that the stop bar 24 moves out of the swiveling area of the magazines 1 when the supply carousel 4 is rotated.

When the door 23 is closed, the supply carousel 4 is rotated about an angle of rotation α, in this case, 36° C., so that the adjacent depositing place 31 comes to a stop in front of the door opening. The door 23 is opened and the next stacking box 3 can be placed on top. This movement sequence can be repeated until the supply carousel 4 is completely loaded, i.e., until all receiving places are occupied by a stacking box 3. The receiving place to be occupied is secured in position relative to the door opening by a magnetic holder (not shown) which is disengaged during the rotation of the supply carousel 4.

The automatic tip changer must be exactly positioned relative to the automatic multichannel pipettor 7 for operation. The enclosed supply carousel 4 is located below the automatic multichannel pipettor 7 which stands on a work plate. The axis of rotation of the supply carousel 4 is oriented essentially parallel to the pipette axes of the automatic multichannel pipettor 7. The magazines 1 which are already supported in the supply carousel 4 are accordingly located in a parallel position relative to the position which they will later occupy in the magazine frame 35 at the pipetting head. The lifting group 5 serves to lift the magazines 1 out of their bearing plane in the supply carousel 4 into the mounting plane. The sliding group 6 is provided for displacing the magazines 1 in the mounting plane into the mounting position (supported on the magazine frame 35).

Figure 5A:
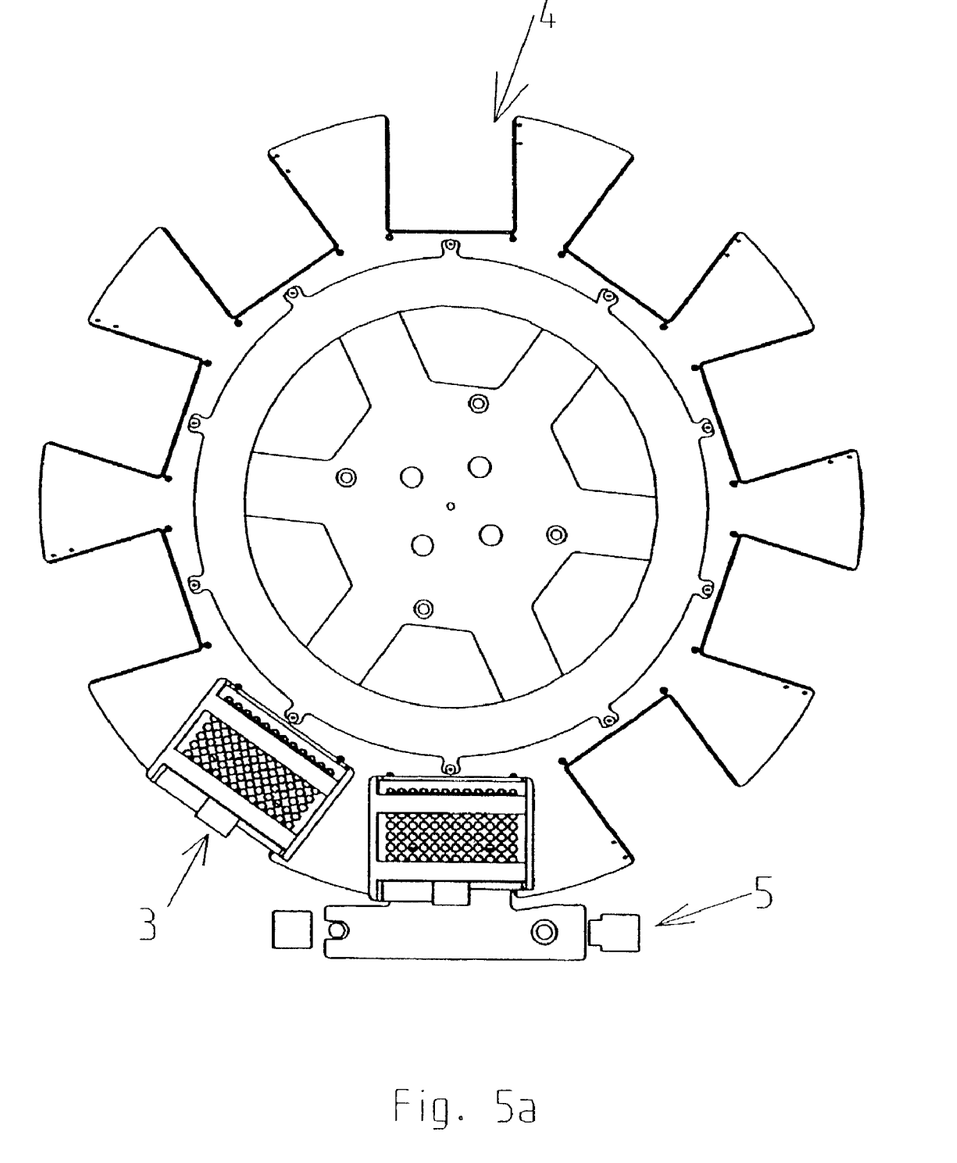
FIG. 5a shows a supply carousel according to FIG. 3a outfitted with two stacking boxes and a lifting group.
Figure 5B:
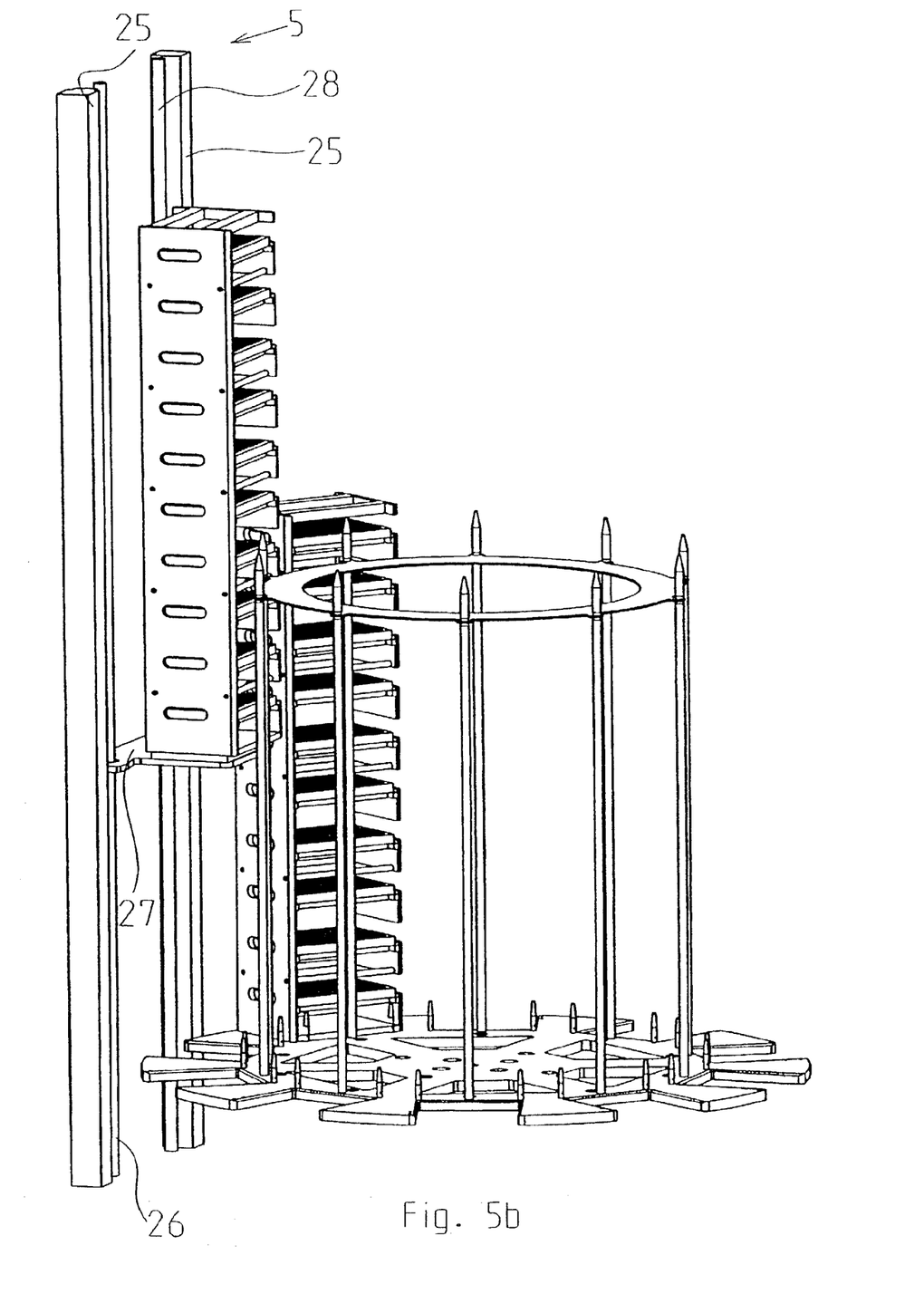
FIG. 5b shows a supply carousel according to FIG. 3b outfitted with two stacking boxes and a lifting group.
Figure 5C:
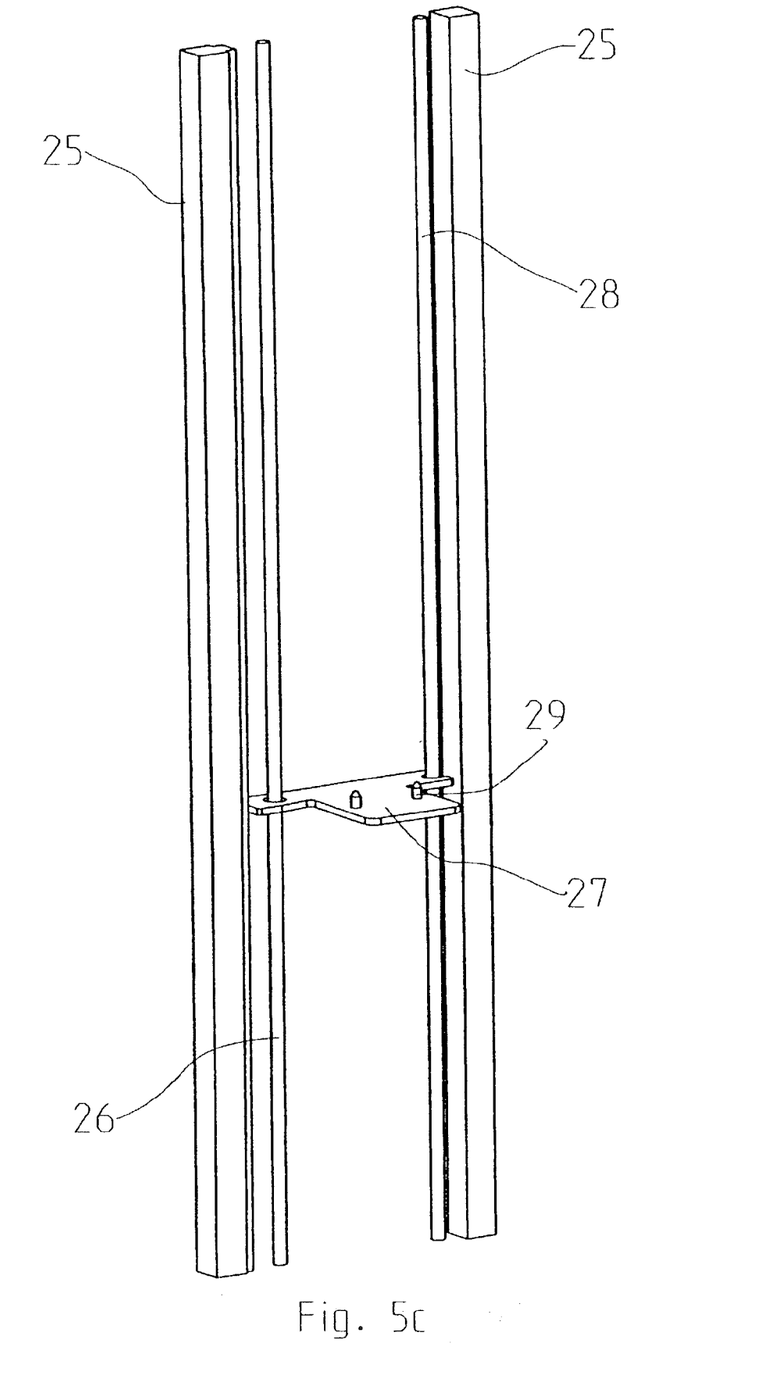
FIG. 5c shows a lifting group.

FIGS. 5a and 5b show a supply carousel 4, which is outfitted with a stacking box 3, in connection with the lifting group 5. FIG. 5c shows the lifting group 5 separately. The lifting group 5 essentially comprises a frame 25, a spindle 26 and a guide bar 28 which are oriented perpendicular to the rotating disk 17 and a spindle drive, not shown, and lifter 27 which is connected with the spindle 26 so as to be displaceable vertically. The lifter 27 is guided on the guide bar 28 so that it does not rotate. The lifter 27 is plate-shaped and has two pins 29 on its upper side.

In order to transport a stacking box 3 from the supply carousel 4 into the mounting area of the automatic multichannel pipettor 7, the spindle 26 is driven and the lifter 27 is lifted. The latter contacts the base plate 16 of a stacking box 3, and the pins 29 engage in the holes that are provided in the base plate 16 for this purpose. The stacking box 3 which is accelerated essentially only in vertical direction during the lift in the mounting area is sufficiently secured in position on the lifter 27 by the pins 29. The stacking box 3 is lifted from the rotating disk 17. As long as magazines 1 are still in contact with one of the stop bars 18 of the supply carousel 4, this stop bar 18 assists in guiding the stacking box 3. As lifting continues, additional auxiliary guide bars, not shown, contact the stacking box 3 in order to prevent tilting or tipping of the stacking box 3. The lifter 27 comes to a stop as soon as the desired magazine 1 is located in the mounting plane. By mounting plane is meant the plane in which a magazine 1 comes to rest on the magazine frame 35 of the pipetting head.

An optical sensor which is directed through a through-hole 15 into the interior of the stacking box 3 is arranged in the mounting plane to the side of the lifting group 5 and detects whether or not a magazine 1 is located in the mounting plane. Further, there is a sensor arrangement which detects a binary-coded bore hole pattern in the second side wall 11 which carries information about the type of magazine, this information being used to regulate the traveling height of the lifter 27.

A barcode 30 (see FIG. 1) is arranged on the magazines 1 and is read out by a barcode reader, not shown. The barcode 30 carries information about the tips 2 in the magazine 1 (e.g., manufacturer, batch, injection tool) and uniquely identifies the magazines, so that monitoring ensures that magazines 1 that have been used once are not used a second time with contaminated tips 2.

After it is used, i.e., after the tips 2 have been contaminated, every magazine 1 is deposited again in the stacking plane from which it was taken. Therefore, the stacking box 3 is advantageously moved into its highest position and the bottom magazine 1 is removed first. This has the advantage that the used magazines 1 always lie below the unused magazines 1. Accordingly, possible dripping from the tips 2 can not result in the contamination of the unused tips 2.

Figure 6A:
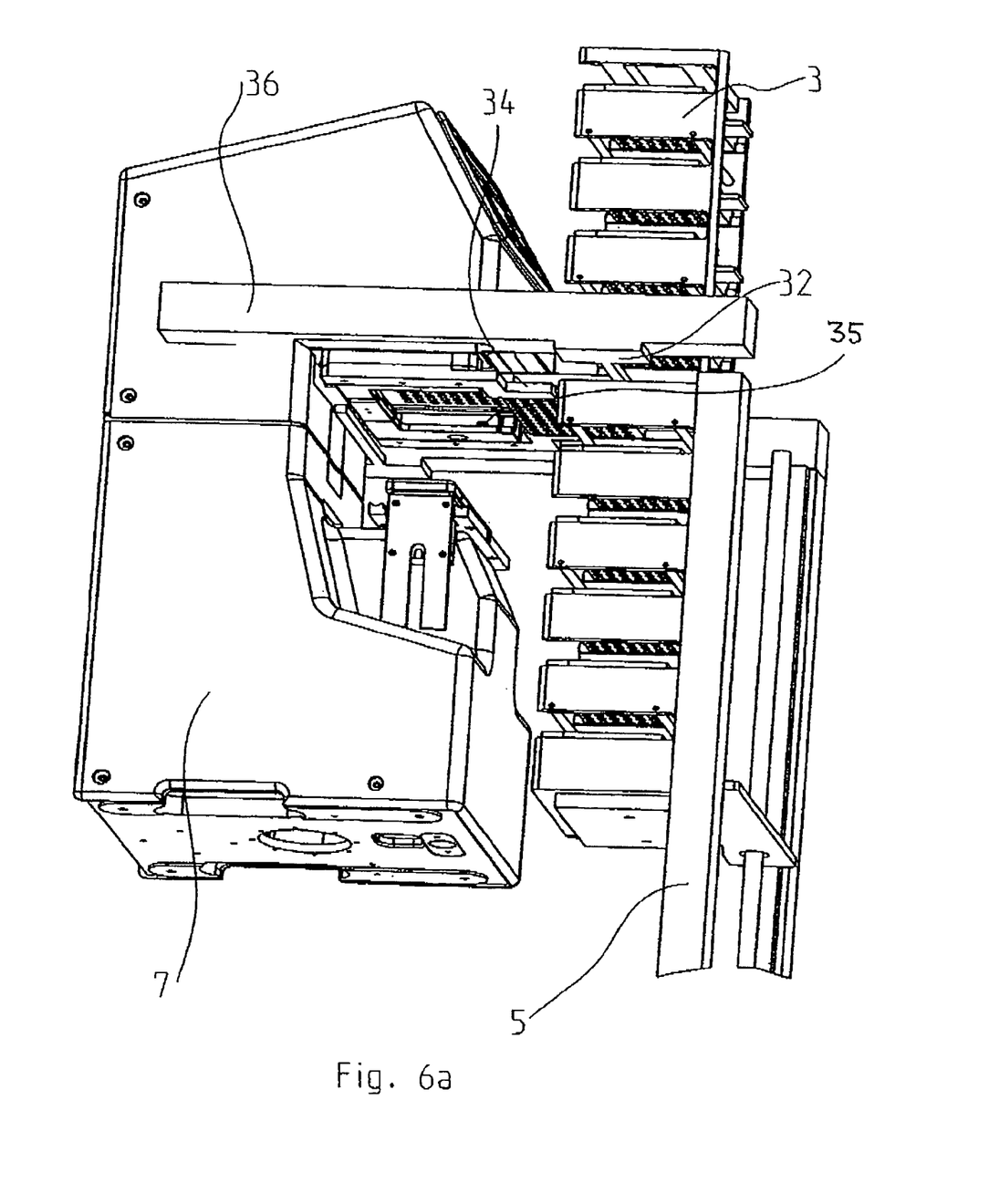
FIG. 6a is a partial view of a tip changer advanced to an automatic multichannel pipettor.
Figure 6B:
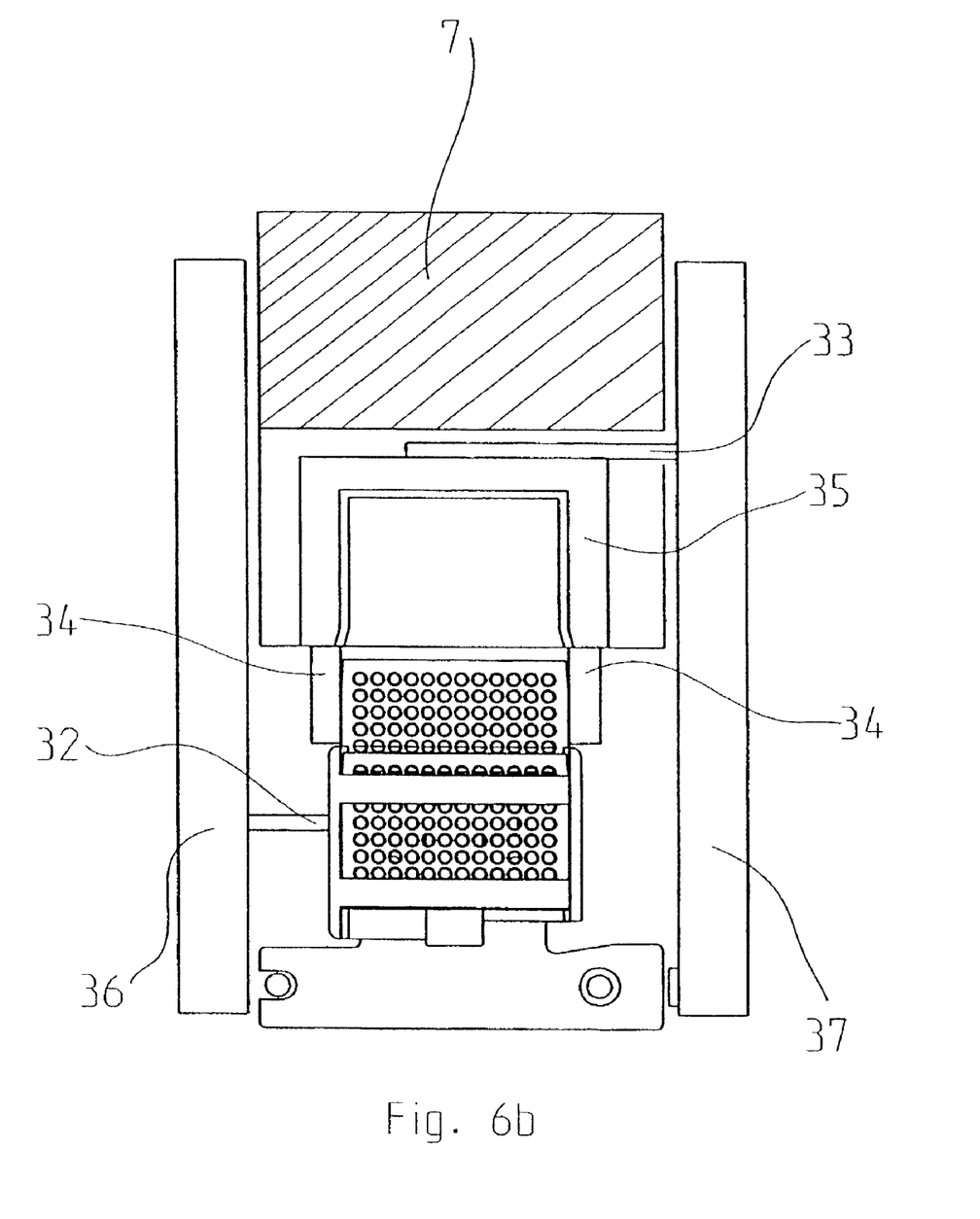
FIG. 6b shows a sliding group with stacking box and magazine frame.
Figure 6C:
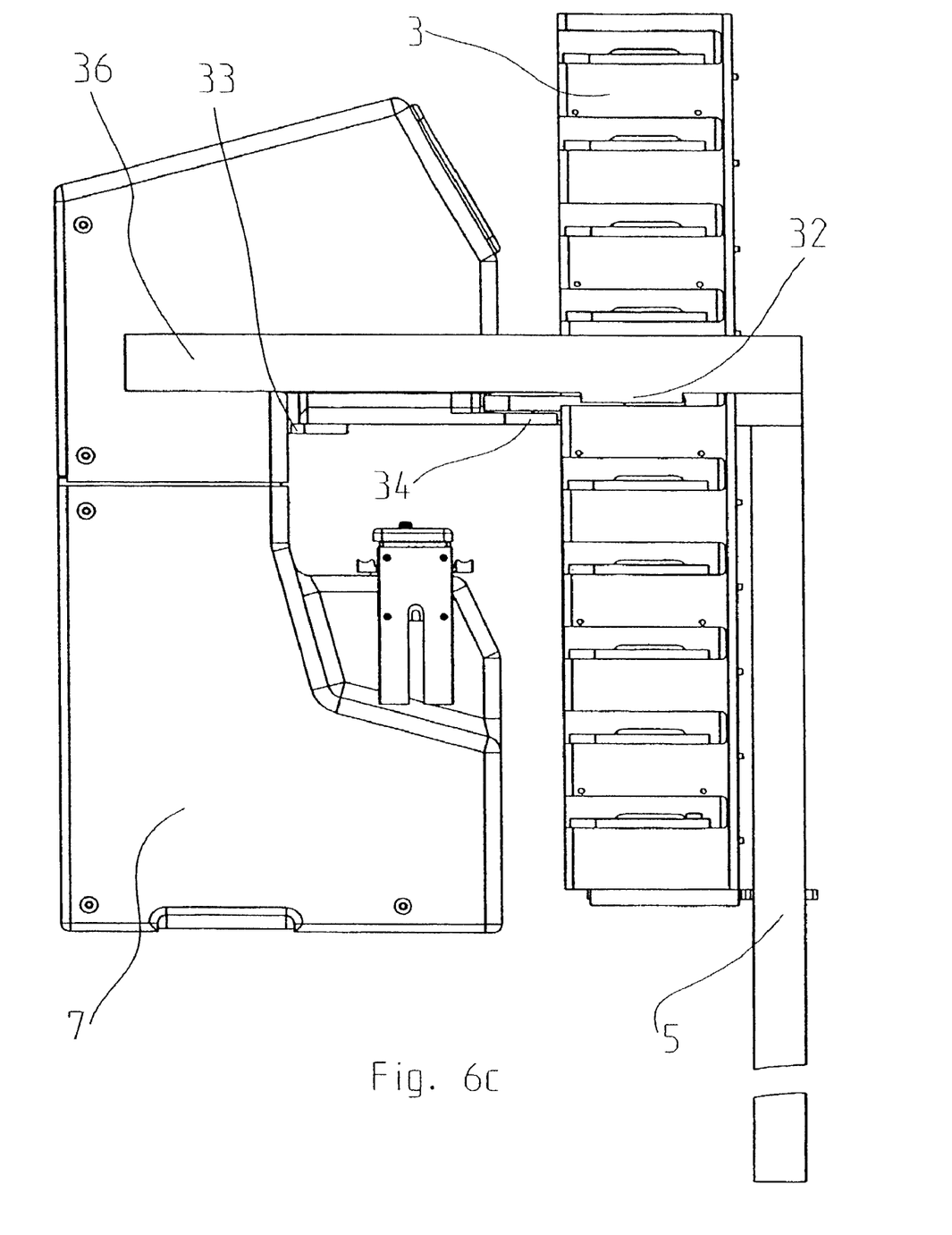
FIG. 6c shows the partial view according to FIG. 6a from the side showing a tip changer advanced to an automatic multichannel pipettor.

The sliding group 6 is used for removing a magazine 1 from the stacking box 3 and depositing it in the magazine frame 35 of the automatic multichannel pipettor 7. In FIG. 6b, the sliding group 6 essentially comprises two pneumatic drives, not shown, each of which is connected to a slide 32, 33 and an auxiliary guide 34 which lengthens the magazine frame 35. The two cylinder-piston arrangements 36, 37, each of which is associated with a pneumatic drive, are arranged orthogonal to the lifting group 5 at the side of the magazine frame 35 and move the slides 32, 33 connected with them into the mounting plane between two end positions. FIGS. 6a and 6b show the sliding group 6 arranged in relation to the automatic multichannel pipettor 7.

The first slide 32 is located in front of the magazine frame 35 of the automatic multichannel pipettor 7 but behind the stacking box 3 (first end position) considered from the lifting group 5 when a stacking box 3 is lifted out. After the stacking box 3 comes to a stop in a position in which the magazine 1 provided for feeding to the automatic multi-channel pipettor 7 is located just below the mounting plane, the first slide 32 is inserted into a slot 14 of the stacking box 3 which is provided for this purpose and moves into its second end position behind the magazine 1 considered from the magazine frame 35. The stacking box 3 is now lifted again by a short distance in order to move the magazine 1 into the mounting plane. The slide 32 is moved to the magazine frame 35 again and carries the magazine 1 along with it. It slides the magazine 1 over the auxiliary guide 34 on the magazine frame 35. The auxiliary guide 34 serves only to bridge the distance between the magazine frame 35 and the guide paths 8 on which the magazines 1 lie in the stacking box 3 and are guided when slid in and out. When the magazine 1 lies in the magazine frame 35, it can be mounted at the pipetting head in the same way as when changing manually.

After the tips 2 are used, the used magazine 1 is exchanged for an unused magazine 1. For this purpose, the used magazine 1 is slid back out of the magazine frame 35 into the stacking box 3 by means of the second slide 33. The magazine 1 is deposited in the same location that it occupied previously. At the same time, the first slide 32 is moved back into its second end position and after the magazine 1 is deposited in the described manner is positioned in its first end position. The cycle described above can be repeated until all magazines 1 in the stacking box 3 are used. The stacking box 3 is then lowered by means of the lifting group 5 and is deposited on a free depositing place 31 of the rotating disk 17. The lifter 27 moves into its neutral position, the supply carousel 4 is rotated by an angle of rotation α and the lifter 27 can lift out the next stacking box 3 in order to transport the magazines 1 into the mounting plane. All drives of the apparatus, such as the pneumatic drives, the spindle drive and the drive for the rotating disk 17, and switches are connected to a computer via a control unit. Outside of the computer, the control unit receives its control signals from sensors such as the optical sensor and the barcode reader for magazine detection.

Laboratory processes are automated to an increased extent with the automatic tip changer in cooperation with automatic multichannel pipettors 7. The laboratory processes are more reliable, faster and less dependent on manpower. Further, an automatic tip changer according to the invention can be retrofitted in existing laboratory setups since it takes up no more space than that required by a manual tip changer in the working area of the previous laboratory installation comprising an automatic multichannel pipettor 7 and additional laboratory equipment which is connected to the latter by transporting paths. FIG. 7 shows a tip changer associated with an automatic multichannel pipettor 7 to which the other laboratory equipment is advanced. The embodiment example described herein is a particularly advantageous embodiment form. Variations in design conceived by persons skilled in the art are intended to be included.

Figure 6D:
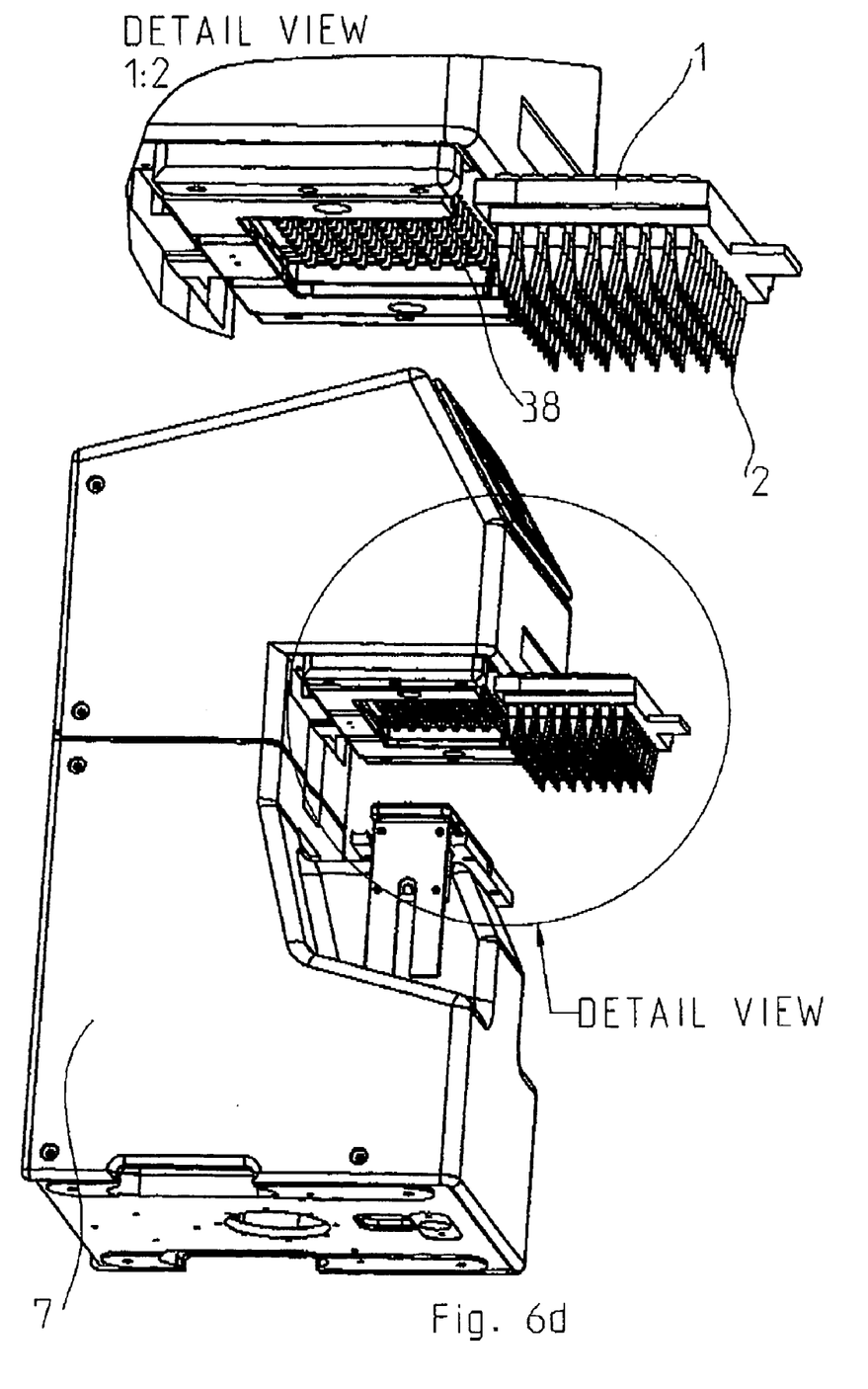
FIG. 6d shows a more detailed view of the pipettes according to one embodiment of the claimed invention.

FIG. 6d illustrates the pipetting head of the automatic multichannel pipettor 7 with a plurality of pipettes 38 arranged so that each of them is connected to each one of tips 2. As illustrated, pipettes 38 are arranged so each of the tips 2 can be connected.

While the foregoing description and drawings represent the present invention, it will be obvious to those skilled in the art that various changes may be made therein without departing from the true spirit and scope of the present invention.

REFERENCE NUMBERS 1 magazine
2 tip
3 stacking box
4 supply carousel
5 lifting group
6 sliding group
7 automatic multichannel pipettor
8 guide path
9 handle
10 first side wall
11 second side wall
12 spacer
13 guide rail
14 slot
15 through-hole
16 base plate
17 rotating disk
18 stop bar
19 fixating ring
20 cutout
21 positioning pin
22 housing
23 door
24 stop bar
25 frame
26 spindle
27 lifter
28 guide bar
29 pin
30 barcode
31 depositing place
32 first slide
33 second slide
34 auxiliary guide
35 magazine frame
36 first cylinder-piston arrangement
37 second cylinder-piston arrangement
$\alpha$ angle of rotation

What is claimed is:

1. An automatic tip changer for an automatic multichannel pipettor comprising:
    a plurality of pipettes arranged in a pipetting head;
    each of the pipettes arranged in the pipetting head being directly connected to a tip;
    a magazine which is outfitted with tips and lying in a magazine frame being pressed against the pipetting head;
    a plurality of stacking boxes in which a plurality of said magazines are stored;
    a supply carousel stores said plurality of stacking boxes in which magazines outfitted with tips are deposited;
    a lifting group means which is arranged in a manner relative to said supply carousel which lifts said plurality of stacking boxes successively from said supply carousel to position the magazines successively in a mounting plane which is determined by the position of the magazine frame; and
    a sliding group means which is arranged in a manner relative to the lifting group and by which each single magazine is displaceable back and forth successively between the stacking box and the magazine frame.

2. The automatic tip changer according to claim 1, wherein the supply carousel comprises a rotating disk with depositing places for the stacking boxes to be deposited, at a first stop bar is allocated to each of the depositing places, one end of the first stop bar being fixedly clamped in the rotating disk and the other end of the first stop bar being fixedly clamped in a fixating ring oriented parallel to the rotating disk, and the first stop bar serves to orient the magazines lying in the stacking boxes.

3. The automatic tip changer according to claim 2, wherein the supply carousel is accommodated in a housing with a door opening and a door at which is located a second stop bar which is oriented parallel to the first stop bar, the second stop bar contacts the magazines lying in a stacking box in a contact pressing position of the door and is located outside a swiveling area of the magazines during rotation of the supply carousel when the door is in a closed position.

* * * * *